United States Patent [19]

McCarty et al.

[11] 4,220,664

[45] * Sep. 2, 1980

[54] DEUTERATED ISOFLURANE AS AN ANESTHETIC AGENT

[75] Inventors: Leslie P. McCarty; Eric R. Larsen, both of Midland, Mich.

[73] Assignee: The Dow Chemical Company, Midland, Mich.

[*] Notice: The portion of the term of this patent subsequent to Feb. 12, 1997, has been disclaimed.

[21] Appl. No.: 7,075

[22] Filed: Jan. 29, 1979

[51] Int. Cl.$^2$ ............................................. A61K 31/08
[52] U.S. Cl. ................................... 424/342; 568/684
[58] Field of Search .......................................... 424/342

[56] References Cited

U.S. PATENT DOCUMENTS

| | | | |
|---|---|---|---|
| 3,535,388 | 10/1970 | Turrell | 424/342 |
| 3,535,425 | 10/1970 | Turrell | 424/342 |
| 4,069,346 | 1/1978 | McCarty | 424/350 |
| 4,131,647 | 12/1978 | McCarty | 424/10 |

*Primary Examiner*—Jerome D. Goldberg

[57] ABSTRACT

Deuterated Isoflurane and anesthetic compositions thereof useful as inhalation anesthetics show reduced levels of inorganic fluoride in urine of anesthetized animals.

5 Claims, No Drawings

DEUTERATED ISOFLURANE AS AN ANESTHETIC AGENT

BACKGROUND OF THE INVENTION

Isoflurane or 1-chloro-2,2,2-trifluoroethyl difluoromethyl ether is an inhalation anesthetic. See U.S. Pat. Nos. 3,535,388 and 3,535,425. Although the metabolic pathways of isoflurane are not well defined, it is known that the compound is metabolized in the body to release inorganic halides into the blood. See Greenstein, et al. *Anesthesiology* 42, 420–424 (1975) and Mazze, et al. *J. Pharmacol. Exptl Therap.* 190, 523–529 (1974). Clinical studies in both laboratory animals and man indicate that the presence of inorganic fluoride in the blood caused by the metabolism of anesthetics containing fluorine is related to renal failure. Therefore, it is desirable to retard the metabolism of an anesthetic containing fluorine, such as isoflurane, to minimize the release of inorganic fluoride into the blood.

SUMMARY OF THE INVENTION

The present invention is directed to the novel deuterated analogue of isoflurane, $CF_3CDClOCF_2H$, or 1-chloro-1-deutero-2,2,2-trifluoroethyl difluoromethyl ether.

The present invention is also directed to a method of anesthetizing an animal, preferably a mammal, which comprises administering by inhalation an effective anesthetizing amount of the compound 1-chloro-1-deutero-2,2,2-trifluoroethyl difluoromethyl ether as a inhalation general anesthetic. As used herein, the term "animal" refers to an inhalation anesthetic susceptible animal.

The present invention is also directed to an anesthetic composition which comprises the minimum alveolar concentration of the compound 1-chloro-1-deutero-2,2,2-trifluoroethyl difluoromethyl ether in combination with an innocuous gas vaporization medium and/or in combination with other anesthetics such as, for example, nitrous oxide. In anesthetizing an animal using the subject compound and methods described herein, the compound is usually administered by vaporizing the compound in the presence of an innocuous gas vaporization medium such as, for example, helium, nitrogen, oxygen, or various mixtures thereof. As used herein, the term "minimum alveolar concentration" refers to the effective concentration of the anesthetic to anesthetize the animal. The particular minimum alveolar concentration depends on factors well known in the art such as the animal to be anesthetized, the particular compound employed, etc.

DETAILED DESCRIPTION OF THE INVENTION

The following examples will serve to further clarify the present invention but are not to be construed as a limitation thereon.

EXAMPLE 1 - PREPARATION OF DEUTERATED ISOFLURANE

The title compound was prepared by charging 100 ml (5.0 moles) of deuterated water, 0.1 mole sodium hydroxide, 0.54 moles of 1-chloro-2,2,2-trifluoroethyl difluoromethyl ether ($CHF_2OCHClCF_3$) and 0.003 moles of tetrabutylammonium hydrogen sulfate into the reaction vessel and heating the mixture at reflux with agitation for six hours. The mixture was allowed to cool to room temperature.

The ether layer was separated, washed with water, dried over calcium chloride and distilled.

The fraction boiling between 48°–49° C. (~52 g) was collected. Gas liquid chromatography showed a single large peak (99.95%) and one trace impurity (<0.05%).

Mass spectral analysis showed the material to be $CF_2H$—$OCHClCF_3$ with 94 percent of the hydrogen of the —OCHCl— group, and 11 percent of the hydrogen of the $CHF_2$— group having been replaced by deuterium.

EXAMPLE 2

Metabolism studies for the presence of inorganic fluorides following the use of deuterated isoflurane and isoflurane were carried out as follows:

A closed circuit exposure chamber was used to anesthetize the test animals. The animals were placed in a 30 liter glass chamber. The air was circulated from the chamber through an ascarite tower by a pump with a capacity of 20 liters per minute. The system was under positive pressure and a 2 liter neoprene bag was used as a reservoir. As oxygen was consumed it was noted by a decrese in the volume of the bag. Pure oxygen was added to the system to maintain it in equilibrium. The temperature in the chamber was monitored and did not exceed 24° C. The anesthetic concentration was monitored by gas chromatography, and the concentration was adjusted by adding liquid through a septum to the air being circulated.

Groups of 6 male Fischer 344 rats (6 months of age, 200–250 grams) were exposed to 2.5% (v/v) isoflurane or 2.5% (v/v) deuterated isoflurane for 2 hours. After exposure, the animals were removed immediately. All animals were maintained in individual metabolism cages for 48 hours after exposure. Urine was collected during each of two 24 hour intervals after exposure. No differences were noted between the anesthetic properties of isoflurane and deuterated isoflurane.

The test animals exposed to isoflurane and the deuterated analog were deeply anesthetized. Two animals treated with isoflurane died during exposure while one of the animals treated with the deuterated analog died. Urinary volume for each surviving animal was recorded and the urine samples were assayed for inorganic fluoride using an Orion fluoride electrode.

A comparison of the amount of total inorganic fluoride in the urine of the control and test animals is shown in Table 1 below.

TABLE 1

| Treatment | Urinary Fluoride ($\eta Eg$) | | Urine Volume in Ml | |
|---|---|---|---|---|
| | At 24 Hrs. | At 48 Hrs. | At 24 Hrs. | At 48 Hrs. |
| Isoflurane | 20.39 ± 8.53 | 9.23 ± 1.79 | 10.1 ± 2.69 | 7.77 ± 1.16 |
| Deuterated Isoflurane | 9.73 ± 2.46 | 6.87 ± 0.80 | 7.47 ± 1.09 | 6.87 ± 0.59 |

The data indicate the deuterated analog produces only about 48% as much fluoride as isoflurane during the first 24 hour interval and about 75% as much during the second 24 hour interval. This indicates a significant reduction in the metabolism of the anesthetic molecule to inorganic fluoride when the deuterated analog is used instead of the undeuterated isoflurane.

We claim:

1. A method for anesthetizing an inhalation anesthetic susceptible animal which comprises administering an effective anesthetizing amount of the compound 1-chloro-1-deutero-2,2,2-trifluoroethyl difluoromethy ether as a inhalation general anesthetic to said animal.

2. The method of claim 2 wherein the compound is administered to the animal in the presence of an innocuous gas vaporizaion medium.

3. The method of claim 2 wherein the compound is administered in the presence of oxygen.

4. An anesthetic composition comprising an effective anesthetizing concentration of the compound 1-chloro-1-deutero-2,2,2-trifluoroethyl difluoromethyl ether and an innocuous gas vaporization medium.

5. The anesthetic composition of claim 4 wherein the innocuous gas vaporization medium is oxygen.

* * * * *